United States Patent [19]

Harr

[11] 4,347,253
[45] Aug. 31, 1982

[54] FUNGICIDES

[75] Inventor: Jost Harr, Oberwil, Switzerland

[73] Assignee: Sandoz Ltd., Basel, Switzerland

[21] Appl. No.: 178,276

[22] Filed: Aug. 15, 1980

[30] Foreign Application Priority Data

Apr. 25, 1980 [GB] United Kingdom ................ 8013719
Apr. 25, 1980 [GB] United Kingdom ................ 8013720
Apr. 25, 1980 [GB] United Kingdom ................ 8013721

[51] Int. Cl.³ .................... A01N 43/36; A01N 43/76; A01N 47/10; A01N 59/20
[52] U.S. Cl. .................... 424/272; 424/141; 424/143; 424/274; 424/286
[58] Field of Search ................ 424/272, 286

[56] References Cited

U.S. PATENT DOCUMENTS 3,591,601  7/1971  Walles ............................. 260/307
3,931,213  1/1976  Kaminski et al. ............... 424/272
4,097,262  6/1978  Cheng ............................. 71/88

FOREIGN PATENT DOCUMENTS 863615  8/1978  Belgium .
871668  2/1979  Belgium .

OTHER PUBLICATIONS

Hauser; Journal of Organic Chemistry 31 (3), pp. 968–970 (1966).
Martin et al.; Pesticide Manual, 5th Ed. pp. 328 & 329.

Primary Examiner—Allen J. Robinson
Attorney, Agent, or Firm—Gerald D. Sharkin; Richard E. Vila

[57] ABSTRACT

The invention provides fungicidal compositions comprising a N-amino-2-oxo-3-oxazolidine derivative (component a) such as 2-methoxy-N-(2,6-dimethylphenyl)-N-(2-oxo-3-oxazolidinyl)-acetamide and a component (b) selected from a copper fungicide, folpet, captan, mancozeb or maneb. A further object of the invention are methods of combating phytopathogenic fungi in plants, seeds or soil with the aid of fungicidally effective amounts of a component (a) and a component (b).

12 Claims, No Drawings

FUNGICIDES

The present invention provides compounds useful in the combating of phytopathogenic fungi.

More specifically the present invention provides compounds of formula I,

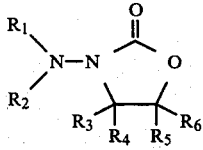

wherein
$R_1$ is

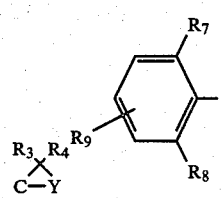

wherein
$R_7$ and $R_8$, independently, are $C_{1-4}$alkyl, halogen or $C_{1-4}$alkoxy, and
$R_9$ is hydrogen, $C_{1-4}$alkyl or halogen, $R_2$ is $CO-R_{10}$, wherein
$R_{10}$ is $C_{1-4}$alkoxy-$C_{1-4}$alkyl, $C_{1-4}$alkylthio-$C_{1-4}$alkyl, 2-furyl, 2-tetrahydrofuryl, halogenated 2-furyl, halogenated 2-tetrahydrofuryl, 1-imidazolylmethyl, 1-pyrrazolylmethyl, 2-tetrahydrofuryloxymethyl, 2-tetrahydropyranyloxymethyl, or $C_{1-4}$halogenalkyl, and
$R_3$, $R_4$, $R_5$ and $R_6$ are independently hydrogen or $C_{1-4}$alkyl.

When any of $R_3$, $R_4$, $R_5$, $R_6$, $R_7$, $R_8$ or $R_9$ is or includes an alkyl group (e.g. alkoxy), this is preferably $C_{1-3}$alkyl, i.e. methyl, ethyl, n-propyl or i-propyl.

When either of $R_7$ or $R_8$ is halogen, this is F, Cl, Br or I, preferably F, Cl or Br, more preferably Cl or Br, particularly Cl.

When any of $R_9$ or $R_{10}$ is or includes halogen this is F, Cl, Br or I, preferably F, Cl or Br, particularly Cl or Br.

Preferred halogenated 2-furyl significances of $R_{10}$ are monohalogenated 2-furyl, e.g. 5-chloro-2-furyl and 5-bromo-2-furyl.

Preferred $C_{1-4}$halogenalkyl significances of $R_{10}$ are $C_{1-4}$chloroalkyl, or $C_{1-4}$bromoalkyl, e.g. chloromethyl, bromomethyl and $C_2H_5CHBr-$.

Preferred halogenated 2-tetrahydrofuryl significances of $R_{10}$ are monohalogenated 2-tetrahydrofuryl, particularly monochlorinated or monobrominated 2-tetrahydrofuryl e.g. 5-chloro-2-tetrahydrofuryl.

Preferred $C_{1-4}$alkoxy-$C_{1-4}$alkyl significances of $R_{10}$ are $C_{1-3}$alkoxymethyl, particularly $CH_3OCH_2-$ and $C_2H_5OCH_2-$.

Preferred $C_{1-4}$alkylthio-$C_{1-4}$alkyl significances of $R_{10}$ are $C_{1-3}$alkylthiomethyl, e.g. $CH_3SCH_2-$.

$R_{10}$ is preferably $C_{1-4}$alkoxy-$C_{1-4}$alkyl, 2-furyl or 5-halo-2-furyl.

When one of $R_3$ and $R_4$ is $C_{1-4}$alkyl, the other is preferably hydrogen.

When one of $R_5$ and $R_6$ is $C_{1-4}$alkyl, the other is preferably hydrogen.

Thus, a preferred group of compounds are the compounds of formula Ia,

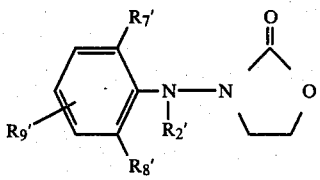

wherein
$R_2'$ is $-COCH_2OCH_3$, $-COCH_2OC_2H_5$, $-CO-(2-furyl)$ or $-CO-(5-halo-2-furyl)$,
$R_7'$ and $R_8'$ independently are $CH_3$, Cl or Br and
$R_9'$ is H, Cl, Br or methyl whereby
$R_7'$ and $R_8'$ are preferably identical.

According to a further aspect of the present invention, the compounds of formula I are produced by intramolecular condensation of a compound of formula II

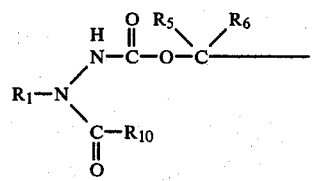

wherein
$R_1$, $R_3$, $R_4$, $R_5$, $R_6$ and $R_{10}$ are as defined above and Y is halogen.

Y is preferably chlorine or bromine, particularly chlorine.

The above intramolecular condensation can be carried out in a conventional manner. The reaction is exothermic. It can e.g. be carried out in a water free medium using as solvent an ether such as dimethoxyethane, an hydrocarbon such as toluene or an other solvent which is inert under the reaction conditions. The reaction temperature is not critical and can lie between about 0° and 100° C. Since the reaction is exothermic one starts the reaction conveniently at room temperature and allows the reaction temperature to rise gradually.

The reaction is conveniently carried out in the presence of an acid binding agent such as sodium hydride, sodium amide or a sodium alcoholate e.g. sodium ethylate.

The intramolecular condensation can also be carried out in an aqueous/organic two-phase system in the presence of an anorganic base e.g. sodium hydroxide and optionally a catalytic amount of a phase transfer catalyst. The organic phase may comprise any appropriate inert water immiscible solvent such as hydrocarbons or halogenated carbons, e.g. xylene, toluene, o-dichloro benzene or dichloromethane. Appropriate phase transfer catalysts are quaternary ammonium compounds such as benzyltrimethyl ammonium bromide, quaternary phosphonium compounds such as benzyltriphenyl phosphonium chloride and crown ethers such as 18-crown-6.

The compounds of formula II are novel. They may be obtained by acylation of compounds of formula III

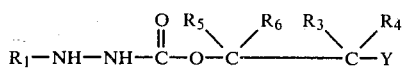
III wherein
R$_1$, R$_3$, R$_4$, R$_5$, R$_6$ and Y are as defined above, with a compound of formula IV,

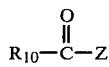
IV wherein
R$_{10}$ is as defined above, and
Z is halogen, particularly Cl, or O—COR$_{10}$,
wherein R$_{10}$ is as defined above.

Suitable solvents for this acylation reaction are hydrocarbons such as toluene or halogenated hydrocarbons such as chlorobenzene. The reaction is conveniently effected at a temperature of from about 50° to about 120° C., e.g. 80° C.

The compounds of formula III may be obtained by conversion of compounds of formula V,

V wherein R$_1$ is as defined above, with a compound of formula VI

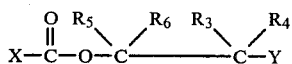
VI wherein
R$_3$, R$_4$, R$_5$, R$_6$ and Y are as defined above, and
X is halogen, particularly Cl.

This conversion may be effected at a temperature of from about 0° to about 10° C. in water or in an organic solvent which is inert under the reaction conditions, conveniently in the presence of a base e.g. an organic amine or sodium hydrogen carbonate.

The starting materials and reagents employed in the processes described above are either known or, insofar as they are not known, they may be produced in analogous manner to the processes described herein or to known processes.

The compounds of formula I have useful fungicidal activity, particularly against phytopathogenic fungi, especially against fungi of the class Oomycetes as indicated by a significant effect in the following tests.

TEST A: Fungicidal effect against *Phytophthora infestans*

Young potted potato plants (3–5 leaf stage) are sprayed with an aqueous spray suspension containing 0.003% (weight/volume) of a compound of formula I, e.g. 2-methoxy-N-(2,6-dimethylphenyl)-N-(2-oxo-3-oxazolidinyl)acetamide (formulated in accordance with Formulation Example I). Two hours later, the treated plants are inoculated with a spore suspension of *Phytophthora infestans* and the plants are then transferred to a tent providing 100% relative atmospheric humidity at an ambient temperature of 16° C. and a day length of 16 hours. Disease control is evaluated 4–5 days later by comparing the treated plants with untreated, similarly inoculated plants. With the above test compound, substantial control of the fungal infestation is observed without any sign of phytotoxicity on the host plants.

TEST B: Fungicidal effect against *Plasmopara viticola*

Young potted plants of grape vine (3–6 leaf stage) are sprayed with an aqueous spray suspension containing 0.0008% (weight/volume) of a compound of formula I, e.g. 2-methoxy-N-(2,6-dimethylphenyl)-N-(2-oxo-3-oxazolidinyl)acetamide (formulated in accordance with Formulation Example I). Two hours later, the treated plants are inoculated with a spore suspension of *Plasmopara viticola* and the plants are then transferred to a tent providing 100% relative atmospheric humidity at an ambient temperature of 15°–22° C. (fluctuating over a 24hr-period) and a day length of 16 hours. Disease control is evaluated 6 days after inoculation by comparing the treated plants with untreated, similarly inoculated plants. With the test compound, substantial control of the fungal infection is observed without any sign of phytotoxicity on the host plants.

TEST C: Curative fungicidal effect against *Plasmopara viticola*

Young potted plants of grape vine (3–6 leaf stage) are inoculated in the same way as determined in Test B, but the application of the compound, e.g. 2-methoxy-N-(2,6-dimethylphenyl)-N-(2-oxo-3-oxazolidinyl)-acetamide (formulated in accordance with Formulation Example I), follows only after 3 days after inoculation; the incubation conditions are the same as described in Test B. Disease control is evaluated as stated in Test B. With the test compound, substantial control of the fungal infection is observed.

TEST D: Eradicative fungicidal effect against *Plasmopara viticola*

The procedure to evaluate this kind of activity is evaluated as described in Test C, with the exception that the treatment is carried out only 6 days after inoculation, when sporulation on the lower leaf surface is already evident. Disease control evaluated 7 days after application of, e.g., 0.012% of the compound 2-methoxy-N-(2,6-dimethylphenyl)-N-(2-oxo-3-oxazolidinyl)-acetamide (formulated in accordance with Formulation Example I), reveals a stopping effect on already sporulating zones, in that sporulation ceases completely.

TEST E: Translocation in treated leaves of grape vines

Excised leaves of grape vine are treated with an aqueous spray suspension containing 0.012% of a compound of formula I, e.g. 2-methoxy-N-(2,6-dimethylphenyl)-N-(2-oxo-3-oxazolidinyl)-acetamide (formulated in accordance with Formulation Example I), in that only the lower half of such leaves is treated. Two hours after treatment, the whole leaf is inoculated with a spore suspension of *Plasmopara viticola* after which the leaves are incubated in a tent providing 100% atmospheric humidity at conditions as described in Test B. Although only the lower half of the leaves was treated as stated above, with the test compound substantial disease control on the entire leaf inoculated was observed. The same effect was observed, when only the upper half of the leaves was treated. This Test thus shows, that the 2-methoxy-N-(2,6-dimethylphenyl)-N-(-oxo-3-oxazolidinyl)-acetamide (formulated in accordance with Formulation Example I), is distributed within a leaf both acropetally and basipetally.

TEST F: Soil Treatment

In vivo, employing *Pythium aphanidermatum*. The fungus is cultivated in a sterile mixture of sand and corn meal (97:3 v/v) to which water is added in a ratio of about 1:4 (v/v); cultivation lasts for 4 days at 25° C. The fungus is then mixed into a semi-sterile mixture of peat and sand which then is treated with a suspension containing the formulated active ingredient to give a concentration of 10 to 160 ppm (e.g. 10, 40 and 160 ppm) calculated per volume substrate). The substrate is transferred to pots of 5 cm diameter which are seeded with cucumber seeds. The planted pots are incubated at 24° C. and 60-70% relative humidity in an incubation chamber for 7 days, after which disease attack is determined by comparing the number of healthy emerged plants with that in untreated, similarly inoculated check pots. The compound of Example 1, hereinafter, used in the wettable powder formulation given above provides full disease control.

Tests analogous to Test F give similar results with peas and sugar beets.

Each of the compounds listed below in the following Examples is found to possess fungicidal properties indicating their usefulness as fungicides.

Particularly effective fungicidal activity is found in the above tests with the compounds of formula Ia
wherein $R_2'$ is $COCH_2OC_2H_5$, $R_7'$ and $R_8'$ are $CH_3$ and $R_9'$ is H,
wherein $R_2'$ is CO—(2-furyl), $R_7'$ and $R_8'$ are $CH_3$ and $R_9'$ is H,
wherein $R_2'$ is CO—(5-bromo-2-furyl), $R_7'$ and $R_8'$ are $CH_3$ and $R_9'$ is H,
wherein $R_2'$ is $COCH_2OCH_3$, $R_7'$ and $R_8'$ are Cl and $R_9'$ is H,
wherein $R_2'$ is $COCH_2OCH_3$, $R_7'$ and $R_8'$ are $CH_3$ and $R_9'$ is 3—Br
and especially with the compound of formula Ia,
wherein $R_2'$ is $COCH_2OCH_3$, $R_7'$ and $R_8'$ are $CH_3$ and $R_9'$ is H.

The invention therefore also provides a method of combating phytopathogenic fungi, especially of the class Oomycetes, in plants, seeds or soil, which process comprises treating the plants, seeds or soil with a fungicidally effective amount of a compound of formula I.

Fungi of the class Oomycetes, against which the method of the invention is particularly effective, are those of the genus Phytophthora in plants such as potatoes, tomatoes, tobacco, citrus, cacao, rubber, apples, strawberries, vegetables and ornamentals, e.g. *Phytophthora infestans* in potatoes and tomatoes; of the genus *Plasmopara viticola* in grape vines; of the genus Peronospora in plants such as tobacco, e.g. *Peronospora tabacina* in tobacco; of the genus Pseudoperonospora in plants such as hops and cucumber, e.g. *Pseudoperonospora humuli* in hops; of the genus Bremia in plants such as lettuce, e.g. *Bremia lactucae* in lettuce; of the genus Pythium causing damping-off and root rots in a great number of plants, such as vegetables, sugar beets, ornamentals and conifers, e.g. *Pythium aphanidermatum* in sugar beets; of the genus Sclerospora in plants such as sorghum and corn, e.g. *Sclerospora sorghi* in sorghum.

For use in the method of the invention, the amount of the preparation to be employed will vary depending on such factors as the species of fungi to be combated, the time and nature of application and the amount and nature of the compound of formula I employed in the preparation.

However, in general, satisfactory results are obtained when applied to a locus, e.g. on crops or to soil with a dosage rate in the range of from 0.05 to 5 kg, preferably from 0.1 to 3 kg of a compound of formula I/ha treated locus, the application being repeated as required. When employed as a seed dressing, satisfactory results are obtained when applied at a rate of from about 0.05 to 0.5, preferably about 0.1 to 0.3 g compound of formula I/kg seed.

According to a preferred method of the invention the compounds of formula I are used in association with other fungicides which are effective against phytopathogenic fungi. Such a combination having an enhanced or broadened fungicidal activity.

A particularly preferred method of the invention comprises applying to the locus to be treated fungicidally effective amounts of
a component (a) comprising a compound of formula I and of
a component (b) selected from
a component (b1) a copper fungicide or
a component (b2) captan or folpet or
a component (b3) mancozeb or maneb.

Copper fungicides form a well-known class of fungicides in which the copper ion contributes to the fungicide activity.

Examples of copper fungicides suitable for use as component (b1) are copper (II) carbonate, copper (II) calcium sulphate, copper (II) calcium oxychloride, tetracupric oxychloride, Bordeaux mixture, Burgundy mixture, cuprous oxide, cupric hydroxide, copper (II) oxychloride or also copper complexes such as copper triethanolamine hydroxide of the formula [Cu N(CH$_2$CH$_2$OH)$_3$]-(OH)$_2$, commercially available under the Trademark K-Lox, or bis(ethylenediamine)-copper (II) sulphate of the formula [Cu(H$_2$NCH$_2$CH$_2$NH$_2$)$_2$]SO$_4$, commercially available under the Trademark Komeen, and mixtures thereof, particularly cuprous oxide, copper (II) oxychloride, cupric hydroxide and a mixture of copper (II) calcium sulphate and copper (II) oxychloride.

Captan, Folpet, Mancozeb and Maneb are the common names for protective fungicides effective against foliage diseases (Pesticide Manual, 5th Ed., by H. Martin and C. R. Worthing, page 76, 281, 328 and 329 resp.).

The method of this invention wherein component (a) and component (b) are used, is effective against a wide range of phytopathogenic fungi.

Preferably component (a) is applied at a rate of 100-400 g/ha and component (b) at a rate of 200-2000 g/ha.

Preferably the weight ratio of component (a): component (b) is in the range of 1:1 to 1:10, more preferably of 1:2 to 1:10, particularly of 1:2 to 1:7.

The method of the invention wherein component (a) and component (b) are used is particularly effective against phytopathogenic fungi in plants such as potato, tomato, and other Solanaceae, tobacco, citrus, cacao, rubber, apple, strawberry, vegetables and ornamentals, e.g. against fungi of the genus Plasmopara, e.g. *Plasmopara viticola* in grape vine, of the genus Guignardia, e.g. *Guignaridia bidwelli* in grape vine of the genus Phoma in grape vine, of the genus Pseudopeziza, e.g. *Pseudopeziza tracheiphila* in grape vine, of the genus Gloeosporium, e.g. *Gloeosporium ampelophagum* in grape vine of the genus Botrytis in grape vine and lettuce, e.g. *Botrytis cinerea* in grape vine, of the genus Phytophthora, e.g. *Phytophthora infestans* in potato, tomato or other Solanaceae, *Phytophthora parasitica* in tomato or other Solanaceae, *Phytophthora cryptogaea* in tomato and other Solanaceae, *Phytophthora mexicana* in tomato and other Solanaceae, *Phytophthora nicotianae* in tobacco and *Phytophthora palmivora* in rubber or cacao, of the genus Peronospora, e.g. *Peronospora tabacina* in tobacco, of the genus Pseudoperonospora, e.g. *Pseudoperonospora humuli* in hop, of the genus Bremia in plants such as lettuce, e.g. Bremia lactucae, of the genus Pythium, e.g. *Pythium aphanidermatum* in sugar beet, of the genus Alternaria, e.g. *Alternaria solani* in potato, tomato and other Solanaceae, *Alternaria tenuis* in tobacco, of the genus Spondylocladium, e.g. *Spondylocladium atrovirens* in potato, of the genus Rhizoctonia, e.g. *Rhizoctonia solani* in potato, tomato and other Solanaceae, of the genus Cladosporium, e.g. *Cladosporium fulvum* in tomato or other Solanaceae, of the genus Colletotrichum in plants such as cacao or tomato, e.g. *Colletotrichum atramentarium* in tomato or other Solanaceae, of the genus Glomerella, e.g. *Glomerella lycopersici* in tomato and other Solanaceae, of Corticium spp in tomato and other Solanaceae, of the genus Botryodiplodia, e.g. *Botryodiplodia theobromae* in cacao. This method of the invention allows the control of a significantly wider range of fungal diseases than by treatment with only one of the components.

In general, a greater than additive effect of the components is observed, especially after treatment with concentrations of component (a) and component (b) allowing a practically complete, more specifically more than 80%, control of the fungi, particularly when copper (II) oxychloride, cuprous oxide, captan, mancozeb or maneb is used as component (b), and especially when used against phytopathogenic fungi of the order Oomycetes, especially against Oomycetes of the genus Phytophthora, e.g. *Phytophthora infestans*, of the genus Plasmopora, e.g. *Plasmopora viticola*, of the genus Peronospora, e.g. *Peronospora tabacina*, of the genus *Pseudoperonospora*, e.g. *Pseudoperonospora humuli*, of the genus Bremia, e.g. *Bremia lactucae*, and of the genus Pythium, e.g. *Pythium aphanidermatum*.

The method of the invention wherein the components (a) and (b) are used, is especially indicated for combating or preventing fungi in grape vines, tomato and other Solanaceae and in cacao when a component (b) is used, in grape vines when a component (b2) is used and in grape vines, potato, tomato and other Solanaceae, tobacco and hop when a component (b3) is used.

The components (a) and (b) may be employed in formulation form and applied e.g. as a tank mix or separately. They are, however, preferably applied in admixture in the form of an aqueous spray or oil based concentrate.

The useful fungicidal activity obtained after treatment with a component (a) and a component (b) is illustrated by the following tests.

TEST G: Fungicidal effect against *Phytophthora infestans*

The test is carried out as described in Test A, whereby the plants are treated with a tank mix of an aqueous spray suspension containing component (a) and component (b) in concentrations indicated in Tables $A_1$ to $A_6$ below. The disease control is evaluated 4–5 days later by comparing the results with the effect that would be obtained if only an additive effect would arise. A more than additive effect is indicated, as illustrated in the following Tables $A_1$ to $A_6$.

$A_1$

| | | \multicolumn{4}{c}{Component (a) of Example 1 hereinafter (in ppm)} | | | |
|---|---|---|---|---|---|
| | | 0 | 2 | 8 | 32 |
| cuprous oxide[1] (in ppm) | 0 | 0 | 30 | 70 | 90 |
| | 2 | 0 | 40 | 80 | 100 |
| | | | (30) | (80) | (100) |
| | 8 | 20 | 60 | 90 | 100 |
| | | | (45) | (90) | (90) |
| | 32 | 60 | 80 | 100 | 100 |
| | | | (70) | (90) | (95) |

( ) calculated additive effect
[1] in commercially available Copper-Sandoz form

TABLE $A_2$

| | | Component (a) of Example 1 hereinafter (in ppm) | | | |
|---|---|---|---|---|---|
| | | 0 | 2 | 8 | 32 |
| cuprous hydroxide[2] (in ppm) | 0 | 0 | 40 | 80 | 100 |
| | 2 | 0 | 50 | 100 | 100 |
| | | | (40) | (80) | (100) |
| | 8 | 30 | 80 | 100 | 100 |
| | | | (60) | (85) | (100) |
| | 32 | 75 | 90 | 100 | 100 |
| | | | (85) | (95) | (100) |

( ) calculated additive effect
[2] in commercially available Kocide 101 form

TABLE $A_3$

| | | Component (a) of Example 1 hereinafter (in ppm) | | | |
|---|---|---|---|---|---|
| | | 0 | 2 | 8 | 32 |
| FOLPET (in ppm) | 0 | 0 | 30 | 80 | 100 |
| | 2 | 20 | 50 | 100 | 100 |
| | | | (45) | (85) | (100) |
| | 8 | 40 | 80 | 100 | 100 |
| | | | (60) | (90) | (100) |
| | 32 | 70 | 90 | 100 | 100 |
| | | | (80) | (95) | (100) |

( ) calculated additive effect.

TABLE $A_4$

| | | Component (a) of Example 1 hereinafter (in ppm) | | | |
|---|---|---|---|---|---|
| | | 0 | 2 | 8 | 32 |
| CAPTAN (in ppm) | 0 | 0 | 40 | 80 | 100 |
| | 2 | 30 | 70 | 90 | 100 |
| | | | (40) | (80) | (100) |
| | 8 | 20 | 90 | 100 | 100 |
| | | | (50) | (85) | (100) |
| | 32 | 80 | 100 | 100 | 100 |
| | | | (90) | (95) | (100) |

( ) calculated additive effect.

TABLE $A_5$

| | | Component (a) of Example 1 hereinafter (in ppm) | | | |
|---|---|---|---|---|---|
| | | 0 | 2 | 8 | 32 |
| Mancozeb (in ppm) | 0 | 0 | 20 | 80 | 95 |
| | 2 | 20 | 80 | 100 | 100 |
| | | | (35) | (85) | (95) |
| | 8 | 40 | 90 | 100 | 100 |
| | | | (50) | (90) | (100) |
| | 32 | 75 | 95 | 100 | 100 |
| | | | (80) | (95) | (100) |

( ) calculated additive effect.

TABLE A₆

| | | Component (a) of Example 1 hereinafter (in ppm) | | | |
|---|---|---|---|---|---|
| | | 0 | 2 | 8 | 32 |
| Maneb (in ppm) | 0 | 0 | 30 | 70 | 95 |
| | 2 | 30 | 70 | 90 | 100 |
| | | | (50) | (80) | (100) |
| | 8 | 40 | 85 | 100 | 100 |
| | | | (60) | (80) | (100) |
| | 32 | 85 | 100 | 100 | 100 |
| | | | (90) | (95) | (100) |

( ) calculated additive effect.

TEST H: Fungicidal effect against *Plasmopara viticola*

The Test is carried out as described in Test B, whereby the plants are treated with a tank mix of an aqueous spray suspension containing component (a) and component (b) in concentrations indicated in Tables B₁ to B₆ below. The observed effect is given by the following Tables B₁ to B₆.

TABLE B₁

| | | Component (a) of Example 1 hereinafter (in ppm) | | | |
|---|---|---|---|---|---|
| | | 0 | 2 | 8 | 32 |
| cuprous oxide[2] (in ppm) | 0 | 0 | 30 | 70 | 100 |
| | 2 | 10 | 30 | 70 | 100 |
| | | | (35) | (75) | (100) |
| | 8 | 50 | 60 | 100 | 100 |
| | | | (65) | (85) | (100) |
| | 32 | 80 | 85 | 100 | 100 |
| | | | (85) | (95) | (100) |

( ) calculated additive effect
[1] in commercially available Copper-Sandoz form

TABLE B₂

| | | Component (a) of Example 1 hereinafter (in ppm) | | | |
|---|---|---|---|---|---|
| | | 0 | 2 | 8 | 32 |
| cuprous hydroxide[2] (in ppm) | 0 | 0 | 40 | 70 | 100 |
| | 2 | 20 | 40 | 70 | 100 |
| | | | (45) | (75) | (100) |
| | 8 | 40 | 60 | 100 | 100 |
| | | | (60) | (80) | (100) |
| | 32 | 70 | 80 | 100 | 100 |
| | | | (80) | (90) | (100) |

( ) calculated additive effect
[2] in commercially available Kocide 101 form

TABLE B₃

| | | Component (a) of Example 1 hereinafter (in ppm) | | | |
|---|---|---|---|---|---|
| | | 0 | 2 | 8 | 32 |
| FOLPET (in ppm) | 0 | 0 | 40 | 80 | 100 |
| | 2 | 40 | 60 | 100 | 100 |
| | | | (65) | (90) | (100) |
| | 8 | 70 | 80 | 100 | 100 |
| | | | (80) | (95) | (100) |
| | 32 | 100 | 100 | 100 | 100 |
| | | | (100) | (100) | (100) |

( ) calculated additive effect.

TABLE B₄

| | | Component (a) of Example 1 hereinafter (in ppm) | | | |
|---|---|---|---|---|---|
| | | 0 | 2 | 8 | 32 |
| CAPTAN (in ppm) | 0 | 0 | 40 | 70 | 100 |
| | 2 | 0 | 40 | 80 | 100 |
| | | | (40) | (70) | (100) |
| | 8 | 70 | 95 | 100 | 100 |
| | | | (80) | (90) | (100) |
| | 32 | 100 | 100 | 100 | 100 |
| | | | (100) | (100) | (100) |

( ) calculated additive effect.

TABLE B₅

| | | Component (a) of Example 1 hereinafter (in ppm) | | | |
|---|---|---|---|---|---|
| | | 0 | 2 | 8 | 32 |
| Mancozeb (in ppm) | 0 | 0 | 40 | 80 | 100 |
| | 2 | 20 | 60 | 100 | 100 |
| | | | (50) | (85) | (100) |
| | 8 | 70 | 95 | 100 | 100 |
| | | | (80) | (95) | (100) |
| | 32 | 90 | 100 | 100 | 100 |
| | | | (95) | (100) | (100) |

( ) Calculated additive effect.

TABLE B₆

| | | Component (a) of Example 1 hereinafter (in ppm) | | | |
|---|---|---|---|---|---|
| | | 0 | 2 | 8 | 32 |
| Maneb (in ppm) | 0 | 0 | 35 | 80 | 100 |
| | 2 | 20 | 50 | 90 | 100 |
| | | | (50) | (85) | (100) |
| | 8 | 60 | 90 | 100 | 100 |
| | | | (75) | (90) | (100) |
| | 32 | 95 | 100 | 100 | 100 |
| | | | (100) | (100) | (100) |

( ) Calculated additive effect.

The compounds of formula I are conveniently employed as fungicidal compositions in association with agriculturally acceptable carriers or diluents. Such compositions also form part of the present invention. They may contain aside from a compound of formula I as active agent, other active agents, such as fungicides, particularly a fungicide selected from the group comprised by component (b) as defined hereinbefore. They may be employed in either solid or liquid application forms e.g. in the form of a wettable powder, an emulsion concentrate, a water dispersible suspension concentrate ("flowable"), a dusting powder, a granulate, a delayed release form, incorporating conventional carriers, diluents and/or adjuvants. Such compositions may be produced in conventional manner.

The compositions of the invention comprising both components (a) and (b) may for example be obtained by mixing said components (a) and (b), optionally with a carrier and other formulating ingredients.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent, said active agent consisting either of at least one compound of formula I or mixtures thereof with other active agents, such as fungicides e.g. a component (b) as defined hereinbefore. Concentrate forms of composition generally contain between about 2 and 80%, preferably between about 5 and 70% by weight of active agent. Liquid application forms of formulation may contain from 0.01 to 20% by weight, preferably from 0.01 to 5% by weight of active agent.

The invention is illustrated by the following Examples wherein parts and percentages are by weight and temperatures are in °C.

FORMULATION EXAMPLE 1: WETTABLE POWDER

50 Parts of 2-methoxy-N-(2,6-dimethylphenyl)-N-(2-oxo-3-oxazolidinyl)-acetamide are ground with 2 parts of lauryl sulphate, 3 parts sodium lignin sulphonate and 45 parts of finely divided kaolinite until the mean particle size is below 5 microns. The resulting wettable powder so obtained is diluted with water before use to a concentration of between 0.01% to 5% active agent. The resulting spray liquor may be applied by foliar spray as well as by root drench application.

FORMULATION EXAMPLE 2: GRANULATE

Onto 94.5 parts by weight of quartz sand in a tumbler mixer is sprayed 0.5 parts by weight of a binder (non-ionic tenside) and the whole thoroughly mixed. 5 Parts by weight of powdered 2-methoxy-N-(2,6-dimethylphenyl)-N-(2-oxo-3-oxazolidinyl)-acetamide are then added and thoroughly mixing continued to obtain a granulate formulation with a particle size in the range of from 0.3 to 0.7 mm. The granulate may be applied by incorporation into the soil adjacent the plants to be treated.

FORMULATION EXAMPLES 3 TO 6 (WETTABLE POWDERS)

| Example | % by weight | | | |
|---|---|---|---|---|
| | 3 | 4 | 5 | 6 |
| Component (a)[1] | 12.65 | 6.25 | 12.5 | 6.25 |
| copper (II) oxychloride (~56% Cu) | 47 | 47 | | |
| cuprous oxide (~88% Cu) | | | 29 | 29 |
| Na laurylsulphate | 1 | 1 | 1 | 1 |
| ligninsulphonate | 10 | 10 | 10 | 10 |
| Kaolin | 29.5 | 35.75 | 39.5 | 45.75 |

[1]e.g. 2-methoxy-N-(2,6-dimethylphenyl)-N-(2-oxo-3-oxazolidinyl)-acetamide

All the components of the formulation are mixed, milled and mixed again in conventional manner.

FORMULATION EXAMPLES 7 TO 9 (WETTABLE POWDERS)

| Example | % by weight | | |
|---|---|---|---|
| | 7 | 8 | 9 |
| Component (a)[1] | 25 | 12.5 | 6.25 |
| Component b2[2] | 50 | 50 | 50 |
| Na oleoylmethyltauride | 2 | 2 | 2 |
| Condensation product of Na alkyl naphthalene-sulphonate and formaldehyde | 5 | 5 | 5 |
| silica gel | 5 | 5 | 5 |
| Kaolin | 13 | 25.5 | 31.75 |

[1]e.g. 2-methoxy-N-(2,6-dimethylphenyl)-N-(2-oxo-3-oxazolidinyl)-acetamide
[2]e.g. Folpet All the components of the formulation are mixed, milled and mixed again in conventional manner.

FORMULATION EXAMPLES 10 TO 12 (WETTABLE POWDERS)

| Example | % by weight | | |
|---|---|---|---|
| | 10 | 11 | 12 |
| Component (a)[1] | 25 | 12.5 | 6.25 |
| Component (b3)[2] | 50 | 50 | 50 |
| Na laurylsulphate | 1 | 1 | 1 |
| ligninsulphonate | 4 | 4 | 4 |
| Silica gel | 5 | 5 | 5 |
| Kaolin | 15 | 27.5 | 33.75 |

[1]e.g. 2-methoxy-N-(2,6-dimethylphenyl)-N-(2-oxo-3-oxazolidinyl)-acetamide
[2]e.g. mancozeb The formulation is obtained by mixing the components, subsequently milling the mixture and repeated mixing in conventional manner.

EXAMPLE 1: 2-Methoxy-N-(2,6-dimethylphenyl)-N-(2-oxo-3-oxazolidinyl)-acetamide 11.8 g (0.0375 mol) 2-Chloroethyl 2-(methoxyacetyl)-2-(2,6-dimethylphenyl)-hydrazinecarboxylate are added portion-wise to a suspension of 2.0 g sodium hydride (in form of about 55% by weight in mineral oil) in 100 ml absolute toluene at room temperature under a blanket of nitrogen. The reaction temperature rises gradually during this addition up to 40°. After the addition is complete the mixture is stirred during 30 minutes without cooling and afterwards cooled to 10°. The unreacted sodium hydride is then destroyed with ethanol, the obtained solution washed with water dried with MgSO$_4$ and the solvent removed in vacuo to give the end title compound which is recrystallised from ethanol to yield the title compound as colourless crystals. m.p. 103°–104°.

EXAMPLE 1a: 2-Chloroethyl 2-(methoxyacetyl)-2-(2,6-dimethylphenyl)-hydrazinecarboxylate The starting material used in Example 1 is obtained as follows:

A mixture of 14.7 g (0.06 mol) of 2-chloroethyl 2-(2,6-dimethylphenyl)-hydrazinecarboxylate and 16.2 g (0.1 mol) methoxy acetic acid anhydride [(CH$_3$OCH$_2$CO)$_2$O] are stirred in 100 ml dry toluene during 1 hour at 80°. After cooling, the solution is washed with water, then with a 5% NaHCO$_3$ aqueous solution and then again with water.

The solution is dried with MgSO$_4$ and the solvent removed in vacuo to give the title compound of Example 1a.

EXAMPLE 1b: 2-Chloroethyl 2-(2,6-dimethylphenyl)-hydrazinecarboxylate

To a mixture of 127 g (0.935 mol) 2,6-dimethyl. phenylhydrazine, 102.5 g (1.3 mol) pyridine and 400 ml water is added, at 0°–5°, 133.5 g (0.935 mol) chloroformic acid β-chloroethyl ester. After the addition is complete, the mixture is stirred for 2 hours at room temperature, the formed precipitate filtered off, washed with water and dried. The so obtained title compound is recrystallised from toluene to yield colourless crystals, m.p. 74°–75°.

According to a preferred alternative procedure of Example 1, 1a and 1b, one proceeds as follows:

EXAMPLE 2: 2-Methoxy-N-(2,6-dimethylphenyl)-N-(2-oxo-3-oxazolidinyl)-acetamide 236.1 g (0.75 mol) 2-Chloroethyl 2-(methoxyacetyl)-2-(2,6-dimethylphenyl)-hydrazinecarboxylate, 375 ml xylene and 187 ml water are stirred with external cooling, while 82.5 ml (0.82 mol) of an aqueous solution of sodium hydroxide (containing ~0.4 g NaOH per ml) are added at a rate to maintain the internal temperature at approx. 20°. The mixture is stirred after completion of the addition for 1 hour at 20°, and for 2 hours at 0°. The solid is filtered off, washed with 150 ml water and dried to yield the title compound as a slightly coloured solid, m.p. 102°–103°.

EXAMPLE 2a: 2-Chloroethyl 2-(methoxyacetyl)-2-(2,6-dimethylphenyl)-hydrazinecarboxylate 200 g (0.825 mol) 2-Chloroethyl 2-(2,6-dimethylphenyl)-hydrazinecarboxylate in 500 ml xylene are warmed to 80°, and added to a warm (80°) solution of 2-methoxyacetylchloride in 250 ml xylene, prepared in situ by treating 73.5 g (0.826 mol) 2-methoxyacetic acid in 250 ml xylene with 107.1 g (0.9 mol) thionyl chloride at 80° for 2 hours. The mixture is heated for 30 minutes at 80°, then worked up as described in Example 1a.

EXAMPLE 2b: 2-Chloroethyl 2-(2,6-dimethylphenyl)-hydrazinecarboxylate

A mixture of 17.7 g (0.1 mol) 2,6-dimethylphenylhydrazine hydrochloride, 21.2 g (0.2 mol) sodium carbonate in 50 ml water and 50 ml xylene are stirred for 30 minutes at room temperature, then cooled to 5°. 14.3 g (0.1 mol) chloroformic acid 2-chloroethylester is then added over a period of 1 hour, the temperature being maintained at 5°. The mixture is stirred at 5° for another hour, at the end of which 100 ml water are added, the precipitate thus formed filtered off, washed with water and dried. Further work-up as in Example 1b.

In analogous manner to that described in the preceding Examples 1 and 2 the following compounds of formula I are produced

| Ex. No. | $R_3$ | $R_4$ | $R_5$ | $R_6$ | $R_7$ | $R_8$ | $R_9$ | $R_{10}$ | M.p. (°C.) |
|---|---|---|---|---|---|---|---|---|---|
| 3 | H | H | H | H | $CH_3$ | $CH_3$ | H | $CH_2OC_2H_5$ | 62–4 |
| 4 | H | H | H | H | $CH_3$ | Cl | H | $CH_2OCH_3$ | 99–100 |
| 5 | H | H | H | H | $CH_3$ | $CH_3$ | H | (furanyl-O) | 190–1 |
| 6 | H | H | H | H | $CH_3$ | $CH_3$ | 4-Cl | $CH_2OCH_3$ | 107–9 |
| 7 | H | $CH_3$ | $CH_3$ | H | $CH_3$ | $CH_3$ | H | $CH_2OCH_3$ | |
| 8 | H | H | H | H | $CH_3$ | $CH_3$ | H | $CH_2SCH_3$ | 113–5 |
| 9 | H | H | H | H | $CH_3$ | $CH_3$ | H | $CH_2Cl$ | 134–6 |
| 10 | H | H | H | H | $CH_3$ | Cl | H | $CH_2Cl$ | 135–6 |
| 11 | H | H | H | H | $CH_3$ | $CH_3$ | H | $CH_2OCH(CH_3)_2$ | |
| 12 | H | H | H | H | $CH_3$ | Cl | H | $CH_2OCH(CH_3)_2$ | |
| 13 | H | H | H | H | $CH_3$ | Cl | H | (furanyl-O) | 166–7 |
| 14 | H | H | H | H | $CH_3$ | $CH_3$ | H | $CH_2SC_4H_9(n)$ | oil |
| 15 | H | H | H | H | $CH_3$ | Cl | H | $CH_2SC_4H_9(n)$ | oil |
| 16 | H | H | H | H | $CH_3$ | $CH_3$ | H | $CH(Br)-C_2H_5$ | 123–4 |
| 17 | H | H | H | H | $CH_3$ | $CH_3$ | H | $CH(Cl)-CH_3$ | 147–8 |
| 18 | H | H | H | H | $CH_3$ | $CH_3$ | H | $CH_2Br$ | 143–4 |
| 19 | H | H | H | H | $CH_3$ | $CH_3$ | H | (furanyl-O, Br) | 119–20 |
| 20 | H | H | H | H | Cl | Cl | H | $CH_2OCH_3$ | 107–9 |
| 21 | H | H | H | H | Cl | Cl | H | $CH_2Cl$ | 142–4 |
| 22 | H | H | H | H | Cl | Cl | H | (furanyl-O) | 173–4 |
| 23 | H | H | H | H | $CH_3$ | $CH_3$ | H | $CH_2N$(imidazolyl) | 139–41 |

-continued

| Ex. No. | R3 | R4 | R5 | R6 | R7 | R8 | R9 | R10 | M.p. (°C.) |
|---|---|---|---|---|---|---|---|---|---|
| 24 | H | H | H | H | CH$_3$ | CH$_3$ | 4-CH$_3$ | CH$_2$OCH$_3$ | oil |
| 25 | H | H | H | H | CH$_3$ | C$_2$H$_5$ | H | CH$_2$Cl | oil |
| 26 | H | H | H | H | CH$_3$ | CH$_3$ | 3-Cl | CH$_2$OCH$_3$ | 90–2 |
| 27 | H | H | H | H | CH$_3$ | CH$_3$ | 3-Br | CH$_2$OCH$_3$ | 96–7 |
| 28 | H | H | H | H | CH$_3$ | CH$_3$ | 3-Br | CH$_2$Cl | 182–3 |
| 29 | H | H | H | H | CH$_3$ | CH$_3$ | 3-Br | 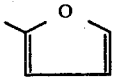 | 145–8 |
| 30 | H | H | H | H | CH$_3$ | Br | 4-CH$_3$ | CH$_2$OCH$_3$ | 125–6 |
| 31 | H | H | H | H | CH$_3$ | Br | 4-CH$_3$ | CH$_2$Cl | 124–6 |
| 32 | H | H | H | H | CH$_3$ | Br | 4-CH$_3$ | 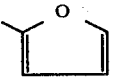 | 193–4 |
| 33 | H | H | H | H | CH$_3$ | CH$_3$ | H | CHOCH$_3$<br>\|<br>CH$_3$ | 90–4 |
| 34 | H | H | H | H | CH$_3$ | CH$_3$ | H | 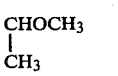 | 149–52 |
| 35 | H | H | H | H | CH$_3$ | CH$_3$ | 4-Cl | CH$_2$Cl | gum |
| 36 | H | H | H | H | CH$_3$ | CH$_3$ | 4-Cl | 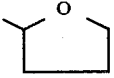 | 164–5 |
| 37 | H | H | H | H | C$_2$H$_5$ | C$_2$H$_5$ | H | CH$_2$OCH$_3$ | 109–12 |
| 38 | H | H | H | H | CH$_3$ | CH$_3$ | H | CH$_2$OC$_3$H$_7$(n) | oil |
| 39 | H | H | H | H | CH$_3$ | CH$_3$ | H | CH$_2$OC$_4$H$_9$(n) | |
| 40 | H | H | H | H | CH$_3$ | CH$_3$ | H | CH$_2$OCH—C$_2$H$_5$<br>\|<br>CH$_3$ | |
| 41 | H | H | H | H | CH$_3$ | CH$_3$ | H | CH$_2$OCH$_2$CH=CH$_2$ | 98–100 |
| 42 | H | H | H | H | CH$_3$ | CH$_3$ | H | CH$_2$OCH$_2$C≡CH | 91–93 |
| 43 | H | H | H | H | CH$_3$ | CH$_3$ | H |  | 107–8 |
| 44 | H | H | CH$_3$ | H | CH$_3$ | CH$_3$ | H | CH$_2$OCH$_3$ | 79–80 |
| 45 | H | H | H | H | CH$_3$ | CH$_3$ | H | 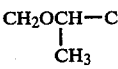 | 56 |
| 46 | H | H | H | H | C$_2$H$_5$ | C$_2$H$_5$ | H | 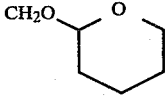 | 142–4 |
| 47 | H | H | H | H | C$_2$H$_5$ | C$_2$H$_5$ | H | CH$_2$Cl | 88–9 |
| 48 | H | H | H | H | Br | Br | H | CH$_2$OCH$_3$ | 150–2 |
| 49 | H | H | H | H | Cl | Cl | 4-Cl | CH$_2$OCH$_3$ | 128–9 |
| 50 | H | H | H | H | C$_2$H$_5$ | C$_2$H$_5$ | 4-Cl | CH$_2$OCH$_3$ | 114–6 |
| 51 | H | H | H | H | Br | Cl | 4-CH$_3$ | CH$_2$OCH$_3$ | 131–4 |
| 52 | H | H | H | H | CH$_3$ | C$_2$H$_5$ | H | CH$_2$OCH$_3$ | 96–8 |
| 53 | H | H | H | H | CH$_3$ | CH$_3$ | 4-Br | CH$_2$OCH$_3$ | 137–8 |

What is claimed is:
1. A fungicidal composition comprising a component a) of formula I

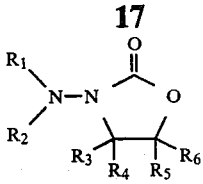

wherein
R₁ is

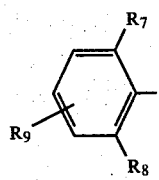

wherein
R₇ and R₈, independently, are $C_{1-4}$alkyl, halogen or $C_{1-4}$alkoxy, and
R₉ is hydrogen, $C_{1-4}$alkyl or halogen,
R₂ is CO-R₁₀,
wherein
R₁₀ is $C_{1-4}$alkoxy-$C_{1-4}$alkyl, $C_{1-4}$alkyl-thio-$C_{1-4}$alkyl, 2-furyl, 2-tetrahydrofuryl, halogenated 2-furyl, halogenated 2-tetrahydrofuryl, 1-imidazolylmethyl, 1-pyrrazolylmethyl, 2-tetrahydrofuryloxymethyl, 2-tetrahydropyranyloxymethyl, $C_{1-4}$halogenalkyl, and
R₃, R₄, R₅ and R₆ are independently hydrogen or $C_{1-4}$alkyl, and
a component (b) selected from the group consisting of mancozeb and maneb; the weight ratio of component a) to component (b) being in the range of 1:1 to 1:10.

2. A fungicidal composition of claim 1, wherein the weight ratio component (a): component (b) is from 1:2 to 1:7.

3. A fungicidal composition of claim 2, in which the component a) is of formula I, defined in claim 1, wherein R₂ is —COCH₂OCH₃, —COCH₂OC₂H₅, —CO—(2-furyl) or —CO—(5-halo-2-furyl), R₃, R₄, R₅ and R₆ are hydrogen, R₇ and R₈ are independently CH₃, Cl or Br and R₉ is H, Cl, Br or CH₃.

4. A composition of claim 3 wherein R₂ is —COCH₂OCH₃, R₃, R₄, R₅ and R₆ are hydrogen, R₇ and R₈ are each methyl and R₉ is hydrogen.

5. A composition of claim 4 wherein component (b) is mancozeb.

6. A composition of claim 4 wherein component (b) is maneb.

7. A method of combating phytopathogenic fungi in a locus which comprises applying to the locus to be treated a fungicidally effective amount of a composition as defined in claim 1.

8. A method according to claim 7 which comprises applying component (a) at a rate of 100–400 g per hectare and component (b) at a rate of 200–2000 g/ha.

9. A method according to claim 8 wherein the weight ratio component (a): component (b) is 1:2 to 1:7.

10. A method according to claim 7 wherein R₂ is —COCH₂OCH₃, R₃, R₄, R₅ and R₆ are hydrogen, R₇ and R₈ are each methyl and R₉ is hydrogen.

11. A method according to claim 10 wherein component (b) is mancozeb.

12. A method according to claim 10 wherein component (b) is maneb.

* * * * *